United States Patent
Sudo et al.

(10) Patent No.: US 6,524,282 B1
(45) Date of Patent: Feb. 25, 2003

(54) SEALING RUBBER CLOSURE FOR SYRINGE/CONTAINER

(75) Inventors: Masamichi Sudo, Tokyo (JP); Morihiro Sudo, Tokyo (JP)

(73) Assignee: Daikyo Seiko, Ltd., Tokyo (JP)

( * ) Notice: Subject to any disclaimer, the term of this patent is extended or adjusted under 35 U.S.C. 154(b) by 15 days.

(21) Appl. No.: 09/641,894

(22) Filed: Aug. 18, 2000

Related U.S. Application Data (62) Division of application No. 09/121,125, filed on Jul. 23, 1998.

(51) Int. Cl.[7] .................................................. A61M 5/00
(52) U.S. Cl. ........................................ 604/263; 604/256
(58) Field of Search ................................. 604/403, 404, 604/407, 408, 411–415, 905, 263, 256, 192, 197; 215/43–45, 50, 247, 250, 277, 355, DIG. 3

(56) References Cited

U.S. PATENT DOCUMENTS

| | | | | |
|---|---|---|---|---|
| 4,366,912 A | * | 1/1983 | Matukura et al. ........... 215/247 |
| 4,915,243 A | * | 4/1990 | Tatsumi et al. .............. 215/247 |
| 5,498,253 A | * | 3/1996 | Aswad et al. ........ 128/DIG. 24 |
| 5,902,298 A | * | 5/1999 | Niedospial et al. ......... 215/247 |
| 5,921,419 A | * | 7/1999 | Niedospial et al. ......... 215/247 |
| 5,971,181 A | * | 10/1999 | Niedospial et al. ......... 215/247 |

* cited by examiner

*Primary Examiner*—Anhtuan T. Nguyen
*Assistant Examiner*—Michael M Thompson
(74) *Attorney, Agent, or Firm*—Oblon, Spivak, McClelland, Maier & Neustadt, P.C.

(57) ABSTRACT

A sealing rubber closure is provided for use with a syringe/container specified by ISO (the International Organization of Standardization) and having a Luer nozzle to be inserted into a Luer-nozzle-receiving part of the sealing rubber closure. The Luer-nozzle-receiving part is configured, on a side of an inner end portion thereof, in an untapered cylindrical form to assure tight-fitted insertion of a free end portion of the Luer nozzle and, on a side of a Luer-nozzle-receiving opening thereof, in a tapered, substantially cylindrical form to assure tight-fitted insertion of a basal end portion of the Luer nozzle. A plastic film is laminated on the sealing rubber closure at least in an area of the Luer-nozzle-receiving part, where a free end of the Luer nozzle is to be maintained in contact with the sealing rubber closure.

9 Claims, 4 Drawing Sheets

SEALING RUBBER CLOSURE FOR SYRINGE/CONTAINER

This is a division of application No. 09/121,125, filed Jul. 23, 1998.

BACKGROUND OF THE INVENTION a) Field of the Invention

The present invention relates to a rubber-made sealing closure (which may also be called a "rubber cap" or "rubber closure") adapted to be fitted on a liquid-medicine-injecting port (Luer nozzle) of a syringe/container with a medicament contained therein so that a solid or liquid injectable preparation contained as the medicament in the syringe/container can be sealed in place to maintain its quality over an extended period of time. The sealing closure has a plastic film laminated thereon at least at an area of an inner wall thereof, where the sealing closure is to be brought into or maintained in contact with the solid or liquid injectable preparation.

b) Description of the Related Art

For medicament containers, especially containers for injectable preparations, strict sealing performance is specified and required as their function in the Pharmacopoeia, to say nothing of the quality of the container material. Accordingly, rubber-made sealing closures in the form of single pieces of rubber without any plastic film laminated thereon have been used because they are considered to be the best in sealing performance.

On the other hand, rubber-made caps which are used with syringes as medical devices are different from sealing rubber closures employed with general containers for injectable preparations such as vials in that the sealing rubber closures normally remain in contact with liquid medicines (the Pharmacopoeia specifies certain quality standards required for the sealing rubber closures).

It is indicated that, when new drugs of these days are brought into direct contact with a rubber material, their active ingredients undergo modifications, thereby making it difficult to maintain their stability over an extended period of time.

Sealing rubber closures for syringe/containers with medicaments filled and sealed therein in advance (which will hereinafter be called "prefilled syringes" on the authority of ISO 11040-1 and the like) are mostly made of a rubber material alone.

An injectable liquid preparation, which has been formulated in a form filled and sealed in a prefilled syringe, always remains in contact with a sealing rubber closure as opposed to an active ingredient in a medicinal preparation contained in a vial (a vessel of small capacity), so that the active ingredient in the injectable liquid preparation in the prefilled syringe tends to receive greater chemical influence from the rubber closure. From the standpoint of protection of the active ingredient from contamination, the conditions under which the active ingredient is placed are severe.

Concerning prefilled syringes themselves, a variety of proposals have been made to date for example, in JP kokai 7-313598 (syringe-shaped container), JP kokai 8-280800 (prefilled syringe for two-part injectable preparation), JP kokai 8-317975 (prefilled syringe and a stopper assembly therefor), and EP 07 09 105A (prefilled syringe and production process of the same). These publications all disclose the structures and function of prefilled syringes, but make no mention whatsoever about the quality and function of sealing rubber closures employed for the sealing of the prefilled syringes.

Figure 2A:
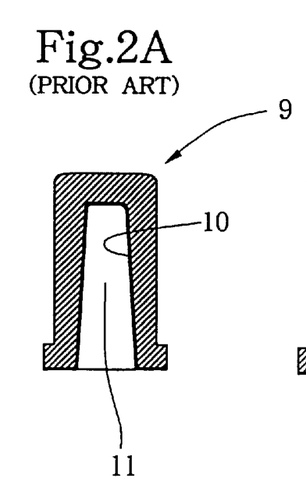
FIG. 2A is a schematic cross-sectional view of a conventional rubber closure.

In connection with rubber closures, on the other hand, the present assignee disclosed in JP kokai 62-139668 (laminated plug for syringe) various examples of rubber-made sliding plugs (plungers) for prefilled syringes, the plugs being laminated at surfaces thereof with tetrafluoroethylene-ethylene copolymer films, and one example of a rubber plug for a front end portion of a syringe (see FIG. 9 in the kokai publication; FIG. 2A in this application). The rubber plug for the front end portion of the syringe, which is disclosed by way of example in the kokai publication, is indicated to be kept out of contact with a liquid medicine owing to the laminated film. Its Luer-nozzle-receiving part (a part in which a liquid-medicine-injecting port is inserted) is configured in a substantially cylindrical, tapered form (i.e., the diameter on a side of an inner end portion is smaller than the diameter on a side of a Luer-nozzle-receiving opening). Accordingly, the Luer nozzle tends to fall out and sealing performance is hardly available, although the Luer-nozzle-receiving part is formed with an average outer diameter smaller than that of the associated Luer nozzle.

Figure 2B:
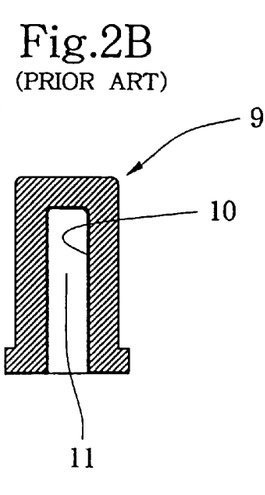
FIG. 2B is a schematic cross-sectional view of another conventional rubber closure.
Figure 2C:
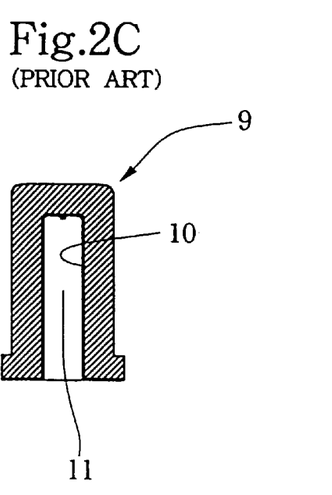
FIG. 2C is a schematic cross-sectional view of a further conventional rubber closure.

With a view to overcoming this problem, the present inventors attempted to close a free end aperture of the Luer nozzle by forming the Luer-nozzle-receiving part of the rubber closure into an untapered cylindrical form (the diameter of which was smaller than the maximum diameter of the Luer nozzle) as shown in FIG. 2B and then forming a small bead on an inner end wall of the Luer-nozzle-receiving part as depicted in FIG. 2C. However, the insertion of the Luer nozzle was not smoothly performed and, when the Luer nozzle was inserted, wrinkles were developed in the laminated film, thereby failing to obtain satisfactory sealing performance.

As has been described above, the conventionally proposed sealing rubber closures in which the front ends of syringes are to be inserted have fluorinated resin films laminated on inner walls thereof, so that the rubber closures are maintained out of direct contact with their corresponding liquid medicines. Since a fluorinated resin has high stiffness and can be hardly deformed, it must inherently apply high fastening force to the Luer nozzle inserted in the rubber closure. However, the inner wall of the rubber closure is formed in a substantially cylindrical form which has substantially the same taper as the Luer nozzle, and the fluorinated resin has small frictional resistance with other materials. Especially in the case of a plastic-made syringe, the inserted Luer nozzle therefore tends to slide. Compared with a rubber closure not laminated with a fluorinated resin film, the rubber closure with the fluorinated resin film laminated thereon is inferior in sealing performance. Therefore, the rubber closure with the fluorinated resin film laminated thereon is not suited for practical use and requires improvements in sealing performance. If the Luer-nozzle-receiving part of the rubber closure is configured in an untapered cylindrical form, on the other hand, the Luer nozzle cannot be inserted smoothly, and wrinkles are hence formed in the laminated film, thereby failing to obtain satisfactory sealing performance.

SUMMARY OF THE INVENTION

With the foregoing circumstances in view, the present inventors have proceeded with an extensive investigation to develop a rubber closure for a prefilled syringe, which has new configurations and function and carries a fluorine resin film or the like laminated on an inner wall thereof so that excellent sealing performance can be achieved like conventional rubber closures without laminated films and any direct contact between a liquid medicine and the material of the rubber closure can be avoided. This investigation has resulted in the completion of the present invention.

To achieve the above object, the present invention provides a sealing rubber closure for use with a prefilled syringe specified by ISO (the International Organization of Standardization) and having a Luer nozzle to be inserted into a Luer-nozzle-receiving part of the sealing rubber closure, wherein the Luer-nozzle-receiving part of the sealing rubber closure is configured, on a side of an inner end portion thereof, in an untapered cylindrical form to assure tight-fitted insertion of a free end portion of the Luer nozzle and, on a side of a Luer-nozzle-receiving opening thereof, in a tapered, substantially cylindrical form to assure tight-fitted insertion of a basal end portion of the Luer nozzle, and a plastic film is laminated on the sealing rubber closure at least in an area of the Luer-nozzle-receiving part, where a free end of the Luer nozzle is to be maintained in contact with the sealing rubber closure.

The present invention also provides a sealing rubber closure similar to the above-described sealing rubber closure, which is for use with a prefilled syringe specified by ISO (the International Organization of Standardization) and having a Luer nozzle and a Luer lock.

According to the present invention, each of the sealing rubber closures, in which a liquid-medicine-injecting portion such as the Luer nozzle of the prefilled syringe is to be inserted, can exhibit both excellent liquid leakproofness and superb gas sealing performance even when its receiving part, where the liquid-medicine-injecting portion is received, is laminated over the entire inner wall thereof with a plastic film.

Similarly to various conventional rubber closures laminated at liquid-medicine-contacting portions thereof with plastic films, the sealing rubber closures according to the present invention can avoid any contact with a liquid medicine so that they do not give any adverse effects to the liquid medicine.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE INVENTION AND PREFERRED EMBODIMENTS

With reference to the accompanying drawings, the present invention will hereinafter be described more specifically on the basis of its preferred embodiments.

Figure 1A:
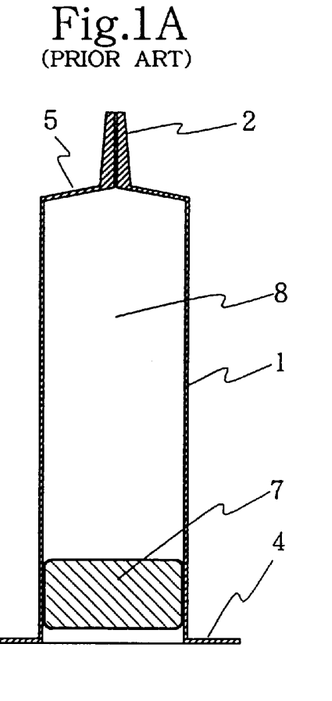
FIG. 1A is a schematic cross-sectional view of a prefilled syringe having only a Luer nozzle.
Figure 1B:
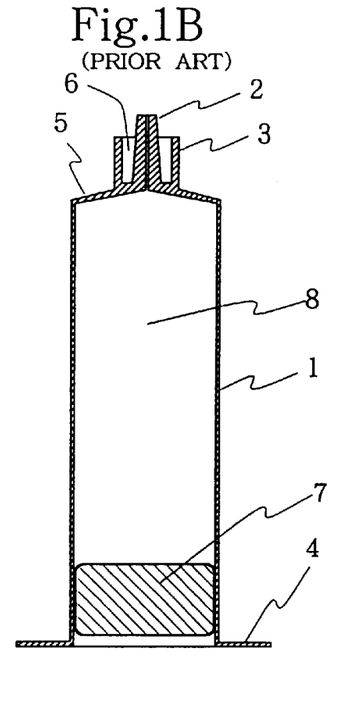
FIG. 1B is a schematic cross-sectional view of a prefilled syringe having a Luer nozzle and a Luer lock.

Schematic cross-sectional views of examples of syringe/containers (prefilled syringes) 8 to which sealing rubber closures 9 according to the present invention are applied are shown in FIG. 1A and FIG. 1B, respectively. Namely, the sealing rubber closures 9 according to the present invention can be applied to a prefilled syringe 8 provided with only a Luer nozzle 2 arranged as a liquid-medicine-injecting portion on a front end wall 5 of the prefilled syringe 8 (FIG. 1A) or to a prefilled syringe 8 provided on a front end wall 5 thereof with a Luer nozzle 2 and a Luer lock 3 for firmly fixing an extension tube, a three-way cock or the like on the prefilled syringe without becoming loose (FIG. 1B, and FIG. 1C which is a perspective view of the Luer nozzle 2 and Luer lock 3). These prefilled syringes 8 are generally made of plastics contain medicament 7, and have base 4.

The shapes and dimensions of the Luer nozzle 2 and the Luer lock 3 in the prefilled syringes are specified by ISO Standards (for example, ISO 594-2, etc.).

In the case of the prefilled syringe 8 shown in FIG. 1B and having the Luer nozzle 2 and the Luer lock 3, for example, the Luer nozzle 2 which is arranged in the form of a hollow cylinder on the front end wall 5 of a syringe barrel 1 is configured to have an about 6/100 taper so that its outer diameter is smaller at a free end portion thereof than at a basal end portion thereof. The Luer lock 3 is in the form of a cylinder arranged concentrically on an outer side of the Luer nozzle 2 and has a helical groove (not shown) formed on an inner wall thereof. An injection needle or the like is screwed in a space 6 between the Luer nozzle 2 and the Luer lock 3 so that the injection needle or the like is maintained in engagement with the prefilled syringe 8. The length of the Luer nozzle 3, the length and inner diameter of the Luer lock 3, and the like are standardized by ISO.

The Luer nozzle 2 is tapered on a peripheral wall thereof as described above. In the conventional sealing rubber closure 9 shown in cross-section in FIG. 2A, a Luer-nozzle-receiving part 11 is therefore configured in a substantially cylindrical form having a slight taper (its average bore diameter is smaller than an average outer diameter of the Luer nozzle 2), and is laminated with a plastic film 10 such as a fluorinated resin film to avoid any direct contact with a medicament 7. Compared with a rubber material, a fluorinated resin has higher stiffness and is hence more resistant to deformation. For its smaller frictional resistance with other materials, however, the tapered Luer nozzle 2 inserted in the sealing rubber closure 9 tends to fall out. It is therefore difficult to maintain sealing performance with a rubber closure 9 laminated with a fluorinated resin film.

When, as is illustrated in FIG. 2B, the receiving part 11 is configured in an untapered cylindrical form having a diameter smaller than the average outer diameter of the Luer nozzle 2 with a view to assuring tight-fitted insertion of the Luer nozzles2, the insertion of the Luer nozzle 2 cannot be performed smoothly, resulting in the development of wrinkles in the laminated plastic film 10 and the failure to obtain sealing performance as described above.

Each rubber closure 9 according to the present invention for being fitted on a Luer nozzle 2 of a prefilled syringe 8 to seal the syringe 8 (which will hereinafter be called simply a "rubber closure") can improve the above-described drawbacks of the conventional rubber closures.

A principal feature of each rubber closure 9 according to the present invention resides in that, as is depicted in FIG. 3A through FIG. 4B, a Luer-nozzle-receiving part 11 of the rubber closure 9 is configured in an untapered cylindrical form on a side of an inner end portion thereof (in an upper portion thereof as viewed in the corresponding drawing) and in a tapered, substantially cylindrical form on a side of a Luer-nozzle-receiving opening 11a thereof (in a lower portion thereof as viewed in the corresponding drawing).

The diameter of the Luer-nozzle-receiving opening 11a of the rubber closure 9 is greater than the outer diameter of the free end portion of the Luer nozzle 2 and the Luer-nozzle-receiving part 11 is configured in the appropriately-tapered cylindrical form to a certain depth from the Luer-nozzle-receiving opening 11a. Accordingly, the insertion of the Luer nozzle 2 into the rubber closure 9 can be performed easily and smoothly while avoiding development of wrinkles in the plastic film 10 laminated on the inner wall of the rubber closure 9. Further, the Luer-nozzle-receiving part 11 is formed, on the side of the inner end portion thereof, in the untapered cylindrical form the inner diameter of which is smaller than the average outer diameter of the free end portion of the Luer nozzle 2. Excellent sealing performance can therefore be maintained.

Concerning rubber closures 9 according to the present invention, a description will first be made about those applied to prefilled syringes 8 liquid-medicine-injecting portions of which consist of Luer nozzles 2 alone. One example of such rubber closures 9 according to the present invention will be described with reference to FIG. 3A, which is its schematic cross-sectional view. A Luer-nozzle-receiving part 11 of the rubber closure 9 is configured, on the side of its inner end portion (the portion above the broken line), in an untapered cylindrical form the diameter of which is smaller than the average outer diameter of the free end portion of the Luer nozzle, said free end portion being to be inserted in the inner end portion, so that the Luer nozzle 2 can be inserted there in a tight-fitted manner. The remaining portion (the portion below the broken line) is configured in a tapered, substantially cylindrical form the average bore diameter of which is somewhat smaller than the average outer diameter of the remaining portion of the Luer nozzle 2, the remaining portion being to be inserted in the former remaining portion, for example, by about 5 to 30%. Further, A plastic film 10 is laminated at least on the inner end wall of the Luer-nozzle-receiving part 11, with which the free end of the Luer nozzle 2 will be maintained in contact. From the standpoint of the production of the rubber closure 9, it is generally preferred to laminate such a plastic film 10 on the entire inner wall of the Luer-nozzle-receiving part 11. This will apply equally to the rubber closures 9 according to the other embodiments of the present invention, which will be described subsequently herein.

Figure 3A:
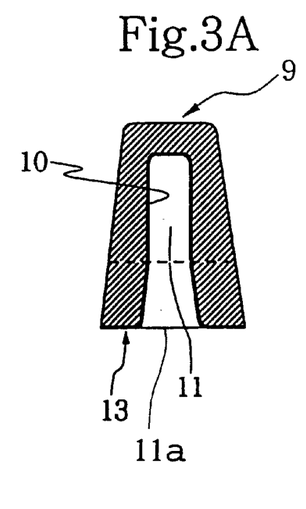
FIG. 3A is a schematic cross-sectional view of a sealing rubber closure according to one embodiment of the present invention.
Figure 3B:
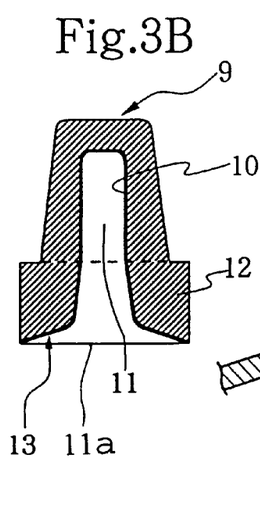
FIG. 3B is a schematic cross-sectional view of a sealing rubber closure according to another embodiment of the present invention.
Figure 3C:
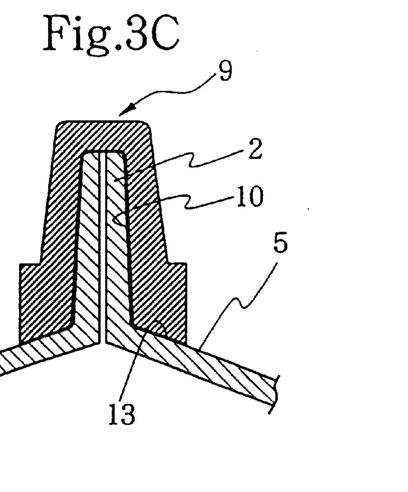
FIG. 3C illustrates the sealing rubber closure of FIG. 3B with a Luer nozzle of a prefilled syringe inserted therein.

As the inner diameter of the Luer-nozzle-receiving opening 11a of the rubber closure 9 according to the present invention is formed greater than the outer diameter of the free end of the Luer nozzle 2 as described above, the insertion of the Luer nozzle 2 into the Luer-nozzle-receiving opening 11a can be facilitated and, when the Luer nozzle 2 is inserted, no wrinkles are developed in the laminated film 10. To further facilitate the insertion of the Luer nozzle 2 into the Luer-nozzle-receiving opening 11a, it is preferred to round an inner peripheral edge portion of the lower end portion 13, in other words, near the Luer-nozzle-receiving opening 11a of the Luer-nozzle-receiving part 11 as shown in FIG. 3B.

Incidentally, the "tapered, substantially cylindrical form" can be embodied in two ways in the present invention, one being the case in which the difference between the bore diameter of the cylindrical Luer-nozzle-receiving part 11 on the side of the inner end portion thereof and that of the Luer-nozzle-receiving part 11 on the side of the Luer-nozzle-receiving opening 11a thereof is small, and the other being the case in which the degree of tapering of the Luer-nozzle-receiving part 11 on the side of the Luer-nozzle-receiving opening 11a is set so that the space of the Luer-nozzle-receiving part 11 takes the form of a combined shape of a frustum of a right circular cone and a right circular cylinder. The expression "tapered, substantially cylindrical form" is used in such a sense as embracing these two cases. This meaning will apply equally to the other rubber closures 9 of the present invention to be described subsequently herein.

Further, the expression "tight-fitted insertion" as used herein means that, as is apparent from the foregoing description, an inserted Luer nozzle 2 or, in the rubber closures 9 of the other embodiments to be described subsequently herein, an inserted Luer lock 3 is firmly fastened by compressive force from a Luer-nozzle-receiving part 11 or Luer-lock-receiving part 14. This meaning will apply equally to the other rubber closures 9 of the present invention.

The untapered cylindrical portion (the portion above the broken line in FIG. 3A or FIG. 3B) of the Luer-nozzle-receiving part 11 has dimensions (length or depth) sufficient to receive at least 30%, preferably 40 to 90%, more preferably 40 to 80% of the length of the Luer nozzle 2, and the remaining portion (the portion below the broken line in FIG. 3A or 3B) of the Luer-nozzle-receiving part 11 is formed in the tapered, substantially cylindrical form.

No particular limitation is imposed on the degree of tapering of the tapered portion of the Luer-nozzle-receiving part 11 (the bore diameter of which is smaller on the side of the inner end portion than on the side of the Luer-nozzle-receiving opening 11a), insofar as the insertion of the Luer nozzle 2 is facilitated. The degree of tapering varies depending on the percentage of the Luer nozzle 2 to be inserted in the Luer-nozzle-receiving part 11, the percentage of the tapered portion based on the Luer-nozzle-receiving part 11, the hardness and thickness of the rubber closure 9, and so on, and can be hardly determined in a wholesale manner. An optimal degree of tapering, therefore, has to be determined by a trial and error method while taking these factors in consideration.

To increase the fastening force for the Luer nozzle 2 so that the sealing performance can be heightened, it is preferred to form at least a portion of the Luer-nozzle-receiving part 11 of the rubber closure, preferably a portion of the rubber closure, the portion extending to at least one fourth (¼), more preferably from one third (⅓) to a half (½) of the overall length of the rubber closure 9 from the lower end of the rubber closure 9, more resistant to deformation than the remaining portion thereof.

No particular limitation is imposed on the external appearance or shape of each rubber closure 9 according to the present invention, but a cylindrical or frustoconical (which means a frustum of a circular cone) shape is preferred from the standpoint of isotropically fastening a Luer nozzle 2 inserted in its Luer-nozzle-receiving part 11. The subsequent description on the wall thickness will be made based on these shapes.

Figure 4A:
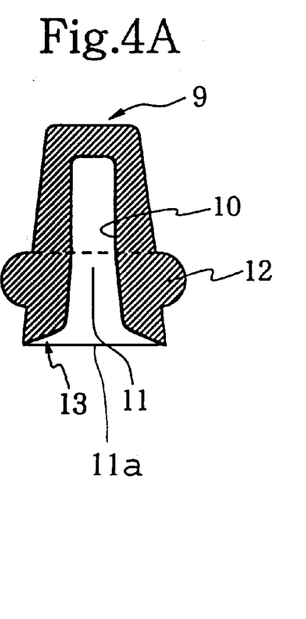
FIG. 4A is a schematic cross-sectional view of a sealing rubber closure according to a further embodiment of the present invention.
Figure 4B:
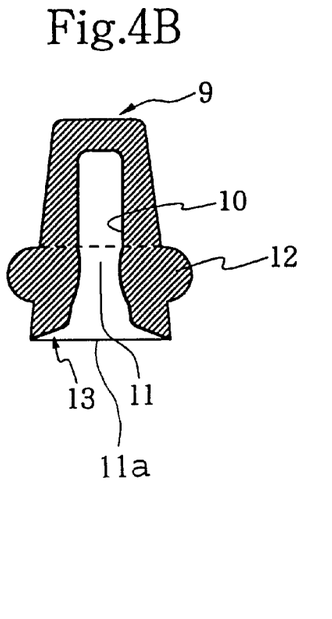
FIG. 4B is a schematic cross-sectional view of a sealing rubber closure according to a still further embodiment of the present invention.

No particular limitation is imposed on the method for making the lower end portion of the rubber closure 9 more resistant to deformation than the remaining portion. As is depicted at numeral 12 in FIG. 3B, for example, it may be mentioned, as a simple method, to make the wall thickness greater on the side of the lower end of the rubber closure 9 than the remaining portion of the rubber closure 9. In general, the preferred average wall thickness of the Luer-nozzle-receiving part 11 may range from 50 to 150% of the average outer diameter of the Luer nozzle 2, and the preferred average wall thickness of the Luer-nozzle-receiving part 11 on the side of the lower end of the rubber closure 9 may be at least 10%, preferably 30 to 200%, more preferably 50 to 150% greater than the average wall thickness of the Luer-nozzle-receiving part11. An increase in the wall thickness by less than 10% cannot bring about any substantial change in sealing performance. On the other hand, even an increase in the wall thickness by more than 200% cannot improve the sealing performance further so that such an excessively large wall thickness is not economical. Incidentally, the portion of such an increased wall thickness extends over the above-described range from the lower end of the rubber closure 9. On a part of this portion, an annular flange of a desired shape such as a semicircular or quadrilateral shape in cross-section may be formed as shown in FIG. 4A. In this modification, the Luer-nozzle-receiving part 11 may be provided with a similar bulged annular portion on the inner wall thereof at a location corresponding to the above-described annular flange.

From the standpoint of further heightening the sealing performance of the rubber closure 9, it is preferred to determine the wall thickness of the Luer-nozzle-receiving part 11 as described above and further to control the hardness (JIS A hardness) of the rubber closure within a range of from 40 to 70, desirably from 55 to 70.

The Luer-nozzle-receiving part 11 of the rubber closure 9 is generally formed with a length (depth) sufficient to permit the insertion of 50% or more of the Luer nozzle 2. When it is formed with a depth sufficient to receive the Luer nozzle 2 in its entirety, the Luer-nozzle-receiving opening 11*a* (lower end) of the rubber closure 9 is brought into contact at least at the inner peripheral edge portion thereof with the front end wall 5 of the prefilled syringe 8. The lower end of the rubber closure 9 is generally configured in the form of a horizontal surface as depicted in FIGS. 2A to 2C. To heighten the sealing performance, however, it is preferred to configure the Luer-nozzle-receiving opening 11*a* of the rubber closure 9 into a shape (surface) complementary with the basal portion of the Luer nozzle 2 or which the Luer-nozzle-receiving opening 11*a* is to be brought into contact, as indicated at numeral 13 in FIG. 3B so that, when the Luer nozzle 2 has been inserted, the lower end surface 13 can be maintained in close contact with the front end wall 5. Even when the length (depth) of the Luer-nozzle-receiving part 11 of the rubber closure 9 is dimensioned shorter (shallower) than the overall length of the Luer nozzle 2 and the lower end of the Luer-nozzle-receiving part 11 is configured in the form of a horizontal surface, it is preferred to provide the inner peripheral edge portion of the lower end of the rubber closure 9 with an adequately rounded portion 13 (FIG. 3A) so that the insertion of the Luer nozzle 2 can be facilitated.

The rubber closures 9 illustrated in FIG. 3A through FIG. 4B are examples of the construction that the Luer-nozzle-receiving part 11 of each rubber closure 9 is formed to a depth sufficient to receive the Luer nozzle 2 over the entire length thereof and is configured in a untapered cylindrical form in a portion thereof extending over 60% the way down from the inner end portion thereof and in a tapered, substantially cylindrical form in the remaining portion thereof, the entire inner wall of the Luer-nozzle-receiving part 11 and the peripheral edge wall of the Luer-nozzle-receiving opening 11*a* are entirely laminated with a plastic film, and the Luer-nozzle-receiving opening 11*a* of the rubber closure 9 (see FIG. 3B, FIG. 4A and FIG. 4B) is configured in a shape maintainable in close contact with the front end wall 5 of the prefilled syringe 8. In these examples, the wall thickness of the Luer-nozzle-receiving part 11 is made greater within the above-described range in a portion thereof extending over 40% the way up from the Luer-nozzle-receiving opening 11*a* (the thickened portions indicated at numeral 12 in FIG. 4A and FIG. 4B) than the remaining portion of the Luer-nozzle-receiving part 11.

A description will next be made about rubber closures 9 according to the present invention, which are suited for use with prefilled syringes 8 liquid-medicine-injecting portions of which are each composed of a Luer nozzle 2 and a Luer lock 3.

One example of the rubber closures 9 will be described based on FIG. 5A which illustrates it in cross-section.

A receiving part of the rubber closure 9 is composed of a Luer-nozzle-receiving part 11 and a Luer-lock-receiving part 14. The Luer-nozzle-receiving part 11 has a depth sufficient to permit the insertion of the Luer nozzle 2 over the entire length thereof (i.e., the entirety of the portion protruding from the free end of the Luer lock 3). and is configured in an untapered cylindrical form having a bore diameter smaller than the average outer diameter of the Luer nozzle 2 at a corresponding location, for example, by about 5 to 30%.

On the other hand, the Luer-lock-receiving part 14 is configured at a portion thereof, which extends over at least 10%, preferably 10 to 40% (to the extent up to the broken line) of the overall length of the Luer-lock-receiving part 14 from a receiving opening 16 of the receiving part of the rubber closure 9, in a tapered, substantially cylindrical form having an average bore diameter smaller than the outer diameter of the Luer lock 3 to be inserted in the portion, for example, by about 5 to 30%. The remaining portion (the portion above the broken line) of the Luer-lock-receiving part 14 is configured in an untapered cylindrical shape having a bore diameter smaller than the outer diameter of the Luer lock 3, for example, by about 5 to 30%.

In general, the outer diameter of the Luer lock 3 is about 5 times as large as the average outer diameter of the Luer nozzle 2. Unless the degree of the above-described tapering is set equal to or greater than the degree of tapering of the outer peripheral surface of the Luer nozzle 2, the insertion of the Luer lock 3 is therefore hampered so that a laminated film 10 may be caused to develop wrinkles. On the other hand, no particular limitation is imposed on the degree of tapering insofar as it facilitates the insertion of the Luer lock 3 into the Luer-lock-receiving part 14. The degree of tapering varies depending on the length of a portion which is provided with a taper. It is necessary to increase the degree of tapering as the length of the tapered portion becomes shorter. Further, the degree of tapering also varies depending on the hardness and wall thickness of the rubber closure 9, that is, the ease of deformation.

It is thus extremely difficult to specify an optimal degree of tapering in a wholesale manner. An optimal degree of tapering, which facilitates the insertion of the Luer lock 3 into the receiving opening 16 and also assures close contact with the Luer lock 3 after the insertion, must be determined by a trial and error method while taking the above-described factors into consideration.

The preferred wall thickness of the Luer-lock-receiving part 14 may be from 30 to 100%, more preferably from 40 to 80% of the outer diameter of the Luer lock 3. Due to the shape of the rubber closure 9 according to the embodiment, the wall thickness of the Luer-nozzle-receiving part 11 unavoidably becomes substantially greater than the wall thickness of the Luer-lock-receiving part 14.

In addition, the receiving part of the rubber closure 9 according to this embodiment is laminated with the plastic film 10 at least in an area where the free end of the Luer nozzle 2 is brought into contact with the rubber closure 9. Laminated locations are the same as those of the rubber closures 9 described above.

Figure 5A:
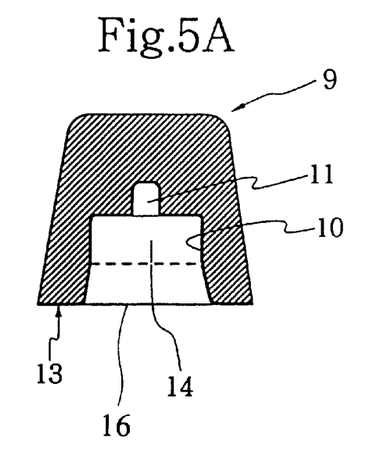
FIG. 5A is a schematic cross-sectional view of a sealing rubber closure according to a still further embodiment of the present invention.
Figure 5B:
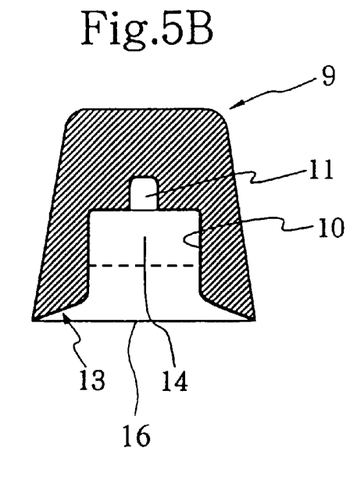
FIG. 5B is a schematic cross-sectional view of a sealing rubber closure according to a still further embodiment of the present invention.
Figure 7:
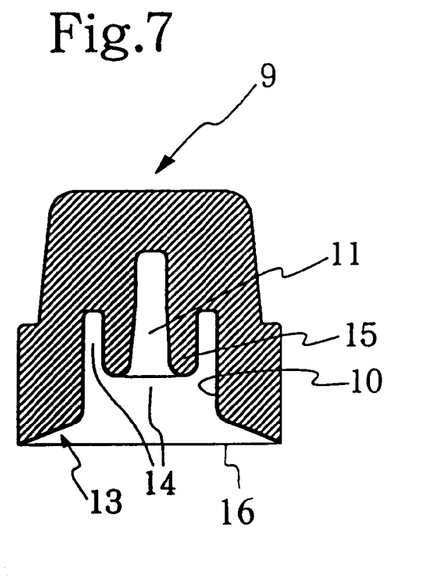
FIG. 7 is a schematic cross-sectional view of a sealing rubber closure according to a still further embodiment of the present invention.

In FIG. 5A, the lower end 13 (near the receiving opening 16) of the rubber closure 9 is configured in the form of a horizontal surface. To facilitate the insertion of the Luer lock 3, it is preferred to provide, as shown in FIG. 5B, the peripheral edge portion of the receiving opening 16 of the rubber closure 9 with an adequate rounded portion 13, for example, a rounded portion similar to the rounded portion in the vicinity of the basal portion of the Luer lock 3. To heighten the sealing performance further, it is preferred, as is illustrated in FIG. 5B, to configure the lower end 13 (near the receiving opening 16) of the Luer-lock-receiving part 11 in a shape maintainable in close contact with the front end wall of the prefilled syringe 8 and/or the basal portion of the Leur lock 3 as in the case of the rubber closures 9 described above. Insofar as the lower end of the rubber closure 9 is configured in a shape maintainable in close contact with the front end wall or the like of a prefilled syringe 8, the insertion of the Luer lock 3 into the receiving opening 16 can be carried out smoothly with extreme ease even if the Luer-lock-receiving part 14 is configured as a whole in an untapered cylindrical form as is depicted in FIG. 7. This makes it possible to avoid development of wrinkles in the laminated film 10 and hence to obtain high sealing performance. FIG. 5B illustrates an example in which the Luer-lock-receiving part 14 is configured as a whole in an untapered cylindrical form.

To further heighten the sealing performance, it is preferred to make at least a portion of the Luer-lock-receiving part 14, the portion extending preferably to at least one fourth (¼), more preferably to one third (⅓) of the overall length of the rubber closure 9 from the lower end of the rubber closure 9, more resistant to deformation than the remaining portion thereof.

No particular limitation is imposed on the method for making the above-mentioned portion more resistant to deformation, but a preferred method is similar to the preferred method described above in connection with the rubber closure 9 of FIG. 3A to FIG. 4B. Namely, it is preferred to make the wall thickness of the above-mentioned portion greater by at least 5%, preferably 10 to 200%, more preferably 40 to 150% than the above-described average wall thickness of the Luer-lock-receiving part 14. An increase in the wall thickness by less than 5% cannot bring about any substantial improvement in sealing performance. On the other hand, even an increase in the wall thickness by more than 200% cannot bring about any additional improvement in sealing performance so that such an excessively large wall thickness is not economical.

In addition, it is also preferred, from the standpoint of heightening sealing performance, to make the hardness of the rubber closure 9 similar to that of the rubber closure 9 described above with reference to FIG. 3A through FIG. 4B.

Figure 6A:
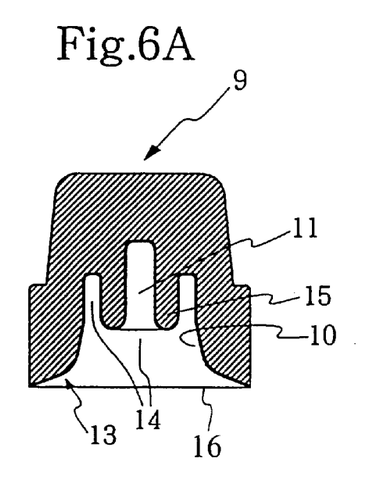
FIG. 6A is a schematic cross-sectional view of a sealing rubber closure according to a still further embodiment of the present invention.
Figure 6B:
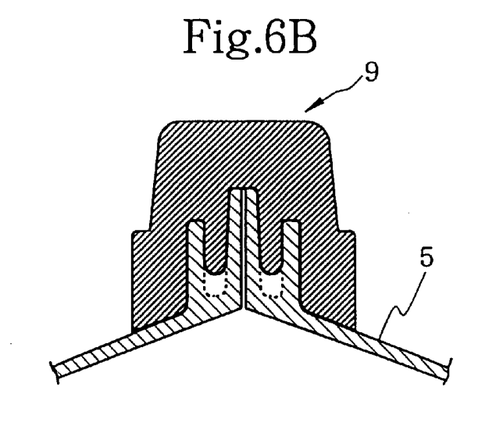
FIG. 6B illustrates the sealing rubber closure of FIG. 6A with a Luer nozzle and Luer lock of a prefilled syringe inserted therein.

In FIG. 6A and FIG. 6B, further examples of rubber closures 9 of this invention for use with prefilled syringes 8 having Luer locks 3 are illustrated in cross-section. Different from the rubber closures 9 shown in FIG. 5A and FIG. 5B, a cylindrical ridge 15 is formed on the side of the inner end portion of the receiving part of a rubber closure 9. The cylindrical ridge 15 is to be inserted in a tight-fitted state not only in a Luer-nozzle-receiving part 11 and a Luer-lock-receiving part 14 but also in an annular space (6 in FIG. 1B) between the Luer nozzle 2 and the Luer lock 3. Except for the cylindrical ridge 15, the rubber closure 9 has the same structure as the rubber closure 9 of FIG. 5A or FIG. 5B. Namely, the space of the Luer-lock-receiving part 14 can be configured in a partly-tapered cylindrical form as in FIG. 5A (FIG. 6A) or in a fully untapered cylindrical form as illustrated in FIG. 5B (FIG. 6B).

Figure 1C:
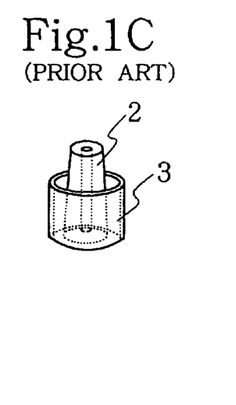
FIG. 1C is a perspective view of the Luer nozzle and Luer lock of the prefilled syringe shown in FIG. 1B.

From the standpoint of sealing performance, it is preferred to make the thickness of the cylindrical ridge 15, which is to be inserted in the annular space (6 in FIG. 1B) greater, for example, by 5 to 20% than the average width of the annular space 6 of the prefilled syringe 8 (see FIG. 1C). The height (length) of the cylindrical ridge 15 may be set at a value sufficient to reach the bottom of the annular space 6, or may be set at such a value that the cylindrical ridge 15 extends only to an intermediate height of the annular space 6. In the latter case (FIG. 6B), it is preferred, for heightened sealing performance, to set the height (length) of the cylindrical ridge 15 at a value equivalent to at least 20% of the depth of the annular space 6.

In the rubber closure 9 shown in FIG. 6A, it is also preferred to provide an inner peripheral edge portion of a receiving opening 16 with a rounded portion 13 similar to that formed in the vicinity of the basal portion of the Luer nozzle 2 so that the rubber closure 9 can be maintained at the inner peripheral edge portion of the lower end 13 thereof in close contact with a basal portion of the Luer lock 3.

A still further embodiment of the present invention is depicted in FIG. 7. A rubber closure 9 of this embodiment, which is for use with a prefilled syringe 8 having a Luer nozzle 2 and Luer lock 3 to be inserted in the rubber closure 9, is configured, at a lower wall 13 surrounding a receiving opening 16 of a Luer-lock-receiving part 14 of the rubber closure 9, a form maintainable in close contact with the basal portion of the Luer lock 3 and a wall of the syringe 8, the wall surrounding the basal portion of the Luer lock 3, and Luer-lock-receiving part 14 is configured as a whole in an untapered cylindrical form.

Figure 8:
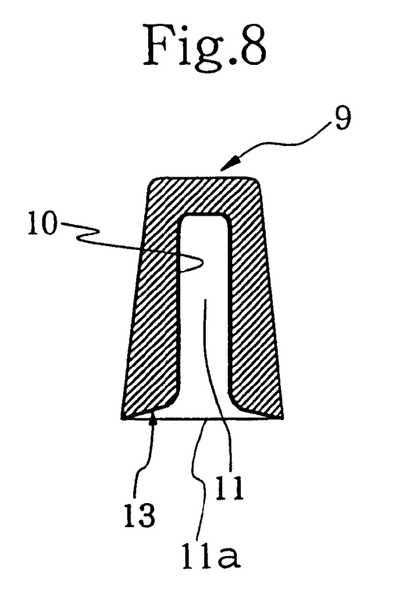
FIG. 8 is a schematic cross-sectional view of a sealing rubber closure according to a still further embodiment of the present invention.

A still further embodiment of the present invention is shown in FIG. 8. A rubber closure 9 of this embodiment, which is for use with a prefilled syringes 8 having a Luer nozzle 2 to be inserted in the rubber closure 9, is configured, at a wall 13 surrounding a Luer-nozzle-receiving opening 11a of a Luer-nozzle-receiving part 11 of the rubber closure 9, in a form maintainable in close contact with the basal portion of the Luer nozzle 2 and a wall of the syringe 8, the wall surrounding the basal portion of the Luer nozzle 2, and the Luer-nozzle-receiving part 11 is configured as a whole in an untapered cylindrical form.

In each of the above-described rubber closures 9 of this invention, a plastic film is laminated on at least a portion of its Luer-nozzle-receiving part 11, which is adapted to receive a free end portion of a Luer nozzle 2 of a prefilled syringe 8 and may be brought into direct contact with a liquid medicine 7 or the like filled in the prefilled syringe 8. No particular limitation is imposed on an area or areas to be laminated other than the above-described laminated portion. A plastic film 10 may be laminated on the entire inner wall of the receiving part 11 or 14 and/or on the peripheral edge portion 13 of the receiving opening 11a or 16.

The above-described rubber closures 9 of, this invention can be produced using a rubber material, a vulcanizer and other additives, which have been used to date for the production of rubber closures 9 for vials. As the liquid medicine 7 filled in the prefilled syringes 8 and the rubber closure 9 are prevented from undergoing direct contact owing to the provision of the plastic film 10, the liquid medicine 7 is free from the potential danger that it could be contaminated by a substance eluted from the rubber closure 9. No limitation is therefore imposed on the kinds, amounts and the like of the rubber material and additives.

Examples of the rubber material can include, but are not limited to, natural rubber (NR), polyisoprene rubber (IR), polybutadiene rubber (BR), styrene-butadiene copolymer rubber (SBR), butyl rubber (IIR), divinylbenzene-copolymerized butyl rubber (XL-IIR), chlorinated or brominated butyl rubber (Cl-IIR, Br-IIR), ethylene-propylene copolymer rubber (EPM), ethylene-propylene-diene monomer terpolymers (EPDMs), acrylonitrile-butadiene copolymer rubber (NBR), and hydrogenated NBR.

Illustrative of the additives are organic peroxide vulcanizer systems (organic peroxides, polyfunctional monomers, etc.), sulfur-containing vulcanizer systems (sulfur or sulfur-yielding compounds, zinc oxide, stearic acid, various vulcanization accelerators, etc.), reinforcing fillers, age resisters, and processing aids. Using a conventional mixer such as a roll mill, Banbury mixer or kneader, these additives and the above-described rubber material are combined into a rubber mix, which is then used for the production of rubber closures 9.

Any plastic film 10 can be used in the present invention insofar as it is inert to (is neither swollen by nor dissolved in) a liquid medicine 7 filled in a prefilled syringe 8. Examples of the plastics can include polyethylene (ordinary molecular weight to ultra-high molecular weight), polypropylene, polycarbonates, polyesters, and fluorinated resins. Particularly preferred are fluorinated resins, including, for example, polytetrafluoroethylene (PTFE), tetrafluoroethylene-ethylene copolymer (ETFE), tetrafluoroethylene-hexafluoropropylene copolymer (FEP), tetrafluoroethylene-fluoroalkyl vinyl ether copolymers (PFAs), polyfluorinated vinylidene (PVDF), and polychlorotrifluoroethylene (PCTFE). These resins are used as sheets or films. No particular limitation is imposed on their thicknesses, but their thicknesses generally range from 1 to 500 µm or so.

Each rubber closure 9 according to the present invention is produced using the above-described mix rubber and plastic film 10, usually, by compression molding, but no particular limitation is imposed on its production method. Upon production by compression molding, for example, top and bottom mold members are used, which have been configured beforehand to define a predetermined shape therebetween. A mix rubber, which is in the form of a sheet and carries one or more plastic films 10 laminated thereon at predetermined areas thereof or over the entire surface thereof, is placed on the lower mold member. The laminate is compressed by the upper mold member and is then heated under elevated pressure to vulcanize the mix rubber, whereby a rubber closure is produced.

The present invention will hereinafter be described specifically by Examples and Comparative Examples.

EXAMPLES 1–3 & COMPARATIVE EXAMPLES 1–4

(1) Production of Rubber Closures

In each Example or Comparative Example, a rubber mix was prepared by mixing and kneading a rubber material and various additives in accordance with the corresponding formulation, which is shown in Table 1, by using a roll mill and an internal mixer. In each of Examples 1–3 and Comparative Examples 3–4, rubber closures for prefilled syringes were produced from this rubber mix and one or more fluorinated resin films (thickness: 50 µm, resin type: ETFE resin) by compression molding. As is shown in Table 2, each of the rubber closures was in a substantially cylindrical form having an average wall thickness of 4.2 mm, and was laminated with the fluorinated resin film at the entire inner wall(s) of its Luer-nozzle-receiving part or its Luer-nozzle-receiving part and Luer-lock-receiving part. In each of Comparative Examples 1–2, non-laminated rubber closures were also produced likewise as shown in Table 2. In all the Examples and Comparative Examples, the vulcanizing conditions were set at 150° C. and 10 minutes.

With respect to the rubber closures so obtained, liquid leakage, gas sealing performance and eluting substance tests were conducted. Methods employed in these tests will be described subsequently herein. Evaluation results are presented in Tables 3 to 5.

TABLE 1

| Rubber material and additives | Formulation A | Formulation B |
| --- | --- | --- |
| Chlorinated butyl rubber (1) | 100 | — |
| Polyisoprene rubber (2) | — | 100 |
| Wet-process silica (3) | 40 | 20 |
| Stearic acid (4) | 0.5 | — |
| Low molecular weight polyethylene (5) | 1 | 1 |
| Zinc white (6) | 3 | — |
| Zinc dimethyldithiocarbamate (7) | 0.4 | — |
| 1,1-(di-t-butylperoxy)-3,3,5-trimethyl-cyclohexane (8) | — | 1.5 |
| Trimethylolpropane trimethacrylate | — | 2 |

(Note)
(1) "Esso Butyl HT-10-66", trade name; product of Japan Butyl Co., Ltd.
(2) "NIPOL IR2200", trade name; product of Nippon Zeon Co., Ltd.

TABLE 1-continued

| Rubber material and additives | Formulation A | Formulation B |
|---|---|---|

(3) "NIPSEAL ER", trade name; product of Nippon Silica Industrial Co., Ltd.
(4) "LUNAC S-30", trade name; product of Kao Corporation.
(5) "HI-WAX #110P", trade name; product of Mitsui Petrochemical Industries, Ltd.
(6) "JIS No. 1 Zinc White", trade name; product of Mitsui Mining & Smelting Co., Ltd.
(7) "AXEL PZ", trade name; product of Kawaguchi Chemical Industry Co., Ltd.
(8) "Perhexa 3M-100", trade name; product of NOF CORPORATION.
(9) "Acryl Ester TMP", trade name; product of Mitsubishi Rayon Co., Ltd.

2) Evaluation Test

Each syringe was immersed in a beaker filled with a 5 wt.% aqueous solution of glycerin, with its Luer nozzle size directed downward. The beaker with the syringe immersed therein was placed in a large vacuum desiccator. The desiccator was maintained at 20 torr (20 mmHg) for 30 minutes, during which the existence or non-existence of air leakage along the rubber closure was observed to evaluate its gas sealing performance. The results are presented in Table 4.

(3) Eluting Substance Test

The "testing method for plastic-made medicament containers" specified in Japanese Pharmacopoeia (JP XIII) was followed.

1) Preparation of Test Solution

TABLE 2

| | Example | | | Comparative Example | | | |
|---|---|---|---|---|---|---|---|
| Rubber closure | 1 | 2 | 3 | 1 | 2 | 3 | 4 |
| Formulation | A | B | B | A | B | A | B |
| Laminated layer | Provided | Provided | Provided | Not provided | Not provided | Provided | Provided |
| Shape | FIG. 3B | FIG. 5A | FIG. 6A | FIG. 3B | FIG. 6A | FIG. 2B | FIG. 5A |
| Luer-nozzle-inserting part Tapered portion/untapered portion | 60/40 | 0/100 | 0/100 | 60/40 | 0/100 | 0/100 | 100/0 |
| Luer-lock-inserting part Tapered portion/untapered portion | Not provided | 50/50 | 0/100 | Not provided | 0/100 | Not provided | 100/0 |

(Note)
"Tapered portion/untapered portion" indicates the percentages of a tapered portion and an untapered portion.

(1) Liquid Leakproofness Test

The liquid leakproofness of each rubber closure for a plastic-made prefilled syringe was evaluated following Method 2 in Appendix D (Measurement of Self-sealing Degree) to the BS (British Standards).

1) Preparation of Test Samples

Ten (10) plastic prefilled syringes of 10 ml capacity were provided for the rubber closures obtained in each of the Examples and Comparative Examples. Each prefilled syringe was sealed at a position close to a flange thereof by a rubber-made plunger with a fluorinated resin film laminated on a surface thereof so that the internal capacity of its barrel became approximately 10 ml. To seal the prefilled syringe, one of the rubber closures was fitted on its Luer nozzle.

2) Testing Method

Each syringe which had been prepared as a test sample in the above was immersed in a large beaker of 500 ml capacity filled with a 0.1 wt.% aqueous solution of methylene blue, with its Luer nozzle side directed downward. The beaker was placed in an autoclave and heated at 121° C. for 30 minutes. After the autoclave was allowed to cool down, the syringe was taken out of the beaker. A sealing portion of the rubber closure was observed to determine whether or not it was contaminated with the blue color of methylene blue, whereby the existence or non-existence of leakage of the filled liquid was determined. The results are presented in Table 3.

(2) Gas Sealing Performance Test

1) Preparation of Test Samples

Same as the preparation of test samples described above under (1)-1).

For the rubber closures obtained in each of the Examples and Comparative Examples, twenty (20) clean syringes of the general purpose type, said syringes having 10 ml capacity, were provided. After each syringe was fitted with a rubber-made plunger of the same type as that descried above, 10 ml of commercial water for injections were injected and filled into the syringe through its Luer nozzle portion by using a commercial silicone-free disposable syringe. With the Luer nozzle side held up, the plunger was gently pushed to drive out air which remained in an end portion of the barrel. One of the rubber closures was fitted on the Luer nozzle to seal the syringe. With the Luer nozzle side held down, the syringe was maintained at 121° C. for 1 hour in an autoclave to conduct elution.

2) Evaluation Test

Each test solution (200 ml), which had been prepared in accordance with the above-described procedures, was collected in a clean conical beaker. Following the testing method for plastic-made medicament containers and the testing method for other aqueous injection containers set out in the Japanese Pharmacopoeia, the test solution was evaluated for changes in chemical properties. The results are presented in Table 5.

TABLE 3

| | Example | | | Comparative Example | | | |
|---|---|---|---|---|---|---|---|
| Liquid leakproofness | 1 | 2 | 3 | 1 | 2 | 3 | 4 |
| Number of leaked sample(s)/number of total samples | 0/10 | 0/10 | 0/10 | 0/10 | 0/10 | 4/10 | 3/10 |

TABLE 4

| Gas sealing performance | Example | | | Comparative Example | | | |
|---|---|---|---|---|---|---|---|
| | 1 | 2 | 3 | 1 | 2 | 3 | 4 |
| Number of leaked sample(s)/number of total samples | 0/10 | 0/10 | 0/10 | 0/10 | 0/10 | 7/10 | 5/10 |

TABLE 5

| Evaluation results | Example | | Comp. Ex. | | Ref. Ex. Commercial water for injections |
|---|---|---|---|---|---|
| | 1 | 2 | 1 | 2 | |
| Reducing substances (ml) [≦2.0] | 0.09 | 0.11 | 0.3 | 0.4 | 0.1 |
| Ultraviolet absorption (transmittance) [≦0.20] | 0.004 | 0.003 | 0.007 | 0.009 | 0.003 |
| Transmission of visible light (%/%) | 100.0/ 100.0 | 100.0/ 100.0 | 99.9/ 99.9 | 98.9/ 99.9 | 100.0/ 100.0 |
| pH value (different from blank) [within ±1.0] | −0.1 | −0.1 | −0.3 | −0.4 | 0 |

From the results presented in Table 5, the sealing rubber closures of the present invention laminated on the entire inner walls of the receiving parts thereof (Examples 1 and 2) are, different from the corresponding non-laminated rubber closures (Comparative Examples 1 and 2), not observed to have substantially affected the liquid medicine (the commercial water for injections was used as the liquid medicine) by their chemical components. It is therefore evident that the sealing rubber closures according to the present invention make it possible to minimize chemical influence which may be given to a medicament during a stability maintenance period (until a deadline for use). In this respect, the sealing rubber closures according to the present invention are the same as the conventional rubber closures having laminated films.

Concerning sealing performance which is an important functional requirement as containers for injectable preparations, it is also clear that the rubber closures according to the present invention are, owing to their shapes, superior in both the liquid leakproofness in Table 3 and the gas sealing performance in Table 4 to the rubber closures of the Comparative Examples.

What is claimed is:

1. A sealing rubber closure and syringe/container system including a sealing rubber closure and a syringe/container, the syringe/container being specified by ISO (the International Organization of Standardization) and having a Luer nozzle and a Luer lock, and the sealing rubber closure and syringe/container system comprising:

a Luer-nozzle-receiving part for receiving a top portion of a free end portion the Luer nozzle of the syringe/container, the Luer-nozzle-receiving part having an untapered, substantially cylindrical sidewall for tight-fitting contact against the top portion of the free end portion of a tapered, substantially cylindrical sidewall of the Luer nozzle of the syringe/container; and a Luer-lock-receiving part including a receiving opening and inner and outer end portions, the inner end portion of the Luer-lock-receiving part being located opposite the receiving opening of the Luer-lock-receiving part and being located adjacent to the Luer-nozzle-receiving part, the outer end portion of the Luer-lock-receiving part being located adjacent to the receiving opening of the Luer-lock-receiving part, the inner end portion of the Luer-lock-receiving part having an untapered, substantially cylindrical sidewall for tight-fitting contact against at least an inner end portion of an untapered, substantially cylindrical sidewall of a free end portion of the Luer lock of the syringe/container when the Luer nozzle and the Luer lock of the syringe/container are both inserted through the receiving opening of the Luer-lock-receiving part and are housed in the Luer-nozzle-receiving part and the Luer-lock-receiving part, respectively, and the outer end portion of the Luer-lock-receiving part having at least a tapered, substantially cylindrical sidewall for face-to-face contact against to a basal end portion of the Luer nozzle and the Luer lock of the syringe/container when the Luer nozzle and the Luer lock of the syringe/container are both inserted through the receiving opening of the Luer-lock-receiving-part and are housed in the Luer-nozzle-receiving part and the Luer-lock-receiving part, respectively.

2. The sealing rubber closure and syringe/container system according to claim 1, wherein the inner end portion of the Luer-lock-receiving part, which has the untapered, substantially cylindrical sidewall, has dimensions sufficient to receive at least one third of a length of the Luer lock.

3. The sealing rubber closure and syringe/container system according to claim 1, wherein said Luer-lock-receiving part is provided on a side of the inner end portion thereof with a ridge which is to be inserted tightly in a space between the Luer lock and the Luer nozzle of the syringe/container.

4. The sealing rubber closure and syringe/container system according to claim 1, further comprising a plastic film lamination on a surface of the Luer-lock-receiving part, wherein the free end portion of the Luer lock are to be maintained in contact with the plastic film lamination at the inner end portion of the Luer-lock-receiving part of the sealing rubber closure.

5. The sealing rubber closure and syringe/container system according to claim 1, wherein the outer end portion of the Luer-lock-receiving part is comprised of first and second sections, the first section being adjacent to the receiving opening and having a tapered, substantially cylindrical sidewall, the second section being adjacent to inner end portion of the Luer-lock-receiving part and having a tapered, substantially cylindrical sidewall which has a degree of taper less than a degree of taper of the tapered, substantially cylindrical sidewall of the first section of the outer end portion of Luer-lock-receiving part.

6. The sealing rubber closure and syringe/container system according to claim 5, wherein the tapered, substantially cylindrical sidewall of the first section of the outer end portion of the Luer-lock-receiving part is approximately parallel to a basal end portion of the free end portions of the Luer nozzle and the Luer lock when the Luer nozzle and the Luer lock are inserted through the receiving opening so that the Luer nozzle and Luer lock are housed in the Luer-nozzle-receiving part and the Luer-lock-receiving part, respectively.

7. The sealing rubber closure and syringe/container system according to claim 6, wherein the tapered, substantially cylindrical sidewall of the second section of the outer end portion of the Luer-lock-receiving part is slightly tapered with respect to the untapered, substantially cylindrical sidewall of the free end portion of the Luer lock when the Luer nozzle and the Luer lock are inserted through the receiving opening so that the Luer nozzle and Luer lock are housed in the Luer-nozzle-receiving part and the Luer-lock-receiving part, respectively.

8. The sealing rubber closure and syringe/container system according to claim 7, further comprising a rounded portion located between the first and second sections.

9. The sealing rubber closure and syringe/container system according to claim 3, wherein the ridge extends into the Luer-lock-receiving part from a wall approximately perpendicular to the untapered, substantially cylindrical sidewall of the inner end portion of the Luer-lock-receiving part.

* * * * *